US009480423B2

(12) United States Patent  
Kim et al.

(10) Patent No.: US 9,480,423 B2
(45) Date of Patent: Nov. 1, 2016

(54) DIAGNOSTIC MEASURING APPARATUS WITH INTEGRATED SPECTROMETER

(75) Inventors: Yoon Ok Kim, Schwerte (DE); Ok-Kyung Cho, Schwerte (DE)

(73) Assignee: Ingo FLORE, Dortmund (DE)

( * ) Notice: Subject to any disclaimer, the term of this patent is extended or adjusted under 35 U.S.C. 154(b) by 346 days.

(21) Appl. No.: 14/111,277

(22) PCT Filed: Apr. 16, 2012

(86) PCT No.: PCT/EP2012/001637
§ 371 (c)(1),
(2), (4) Date: Nov. 20, 2013

(87) PCT Pub. No.: WO2012/139776
PCT Pub. Date: Oct. 18, 2012

(65) Prior Publication Data
US 2014/0081093 A1    Mar. 20, 2014

(30) Foreign Application Priority Data
Apr. 14, 2011    (DE) .......................... 10 2011 017 064

(51) Int. Cl.
*A61B 5/00* (2006.01)
*A61B 5/1455* (2006.01)
*A61B 5/145* (2006.01)

(52) U.S. Cl.
CPC .......... *A61B 5/14552* (2013.01); *A61B 5/0075* (2013.01); *A61B 5/1455* (2013.01); *A61B5/14532* (2013.01); *A61B 5/6826* (2013.01); *A61B 2562/028* (2013.01); *A61B 2562/0238* (2013.01); *A61B 2562/0295* (2013.01); *A61B 2562/046* (2013.01); *A61B 2562/06* (2013.01)

(58) Field of Classification Search
CPC ............ A61B 5/1455; A61B 5/14551; A61B 5/14552; A61B 5/0075; A61B 5/02416; A61B 5/02427; A61B 5/02444; A61B 5/0295; A61B 5/6826; A61B 2562/0238; A61B 2562/028; A61B 2562/0295; A61B 2562/046
See application file for complete search history.

(56) References Cited

U.S. PATENT DOCUMENTS 5,494,032 A * 2/1996 Robinson ........... A61B 5/14542
356/41
5,974,337 A * 10/1999 Kaffka ............... A61B 5/14532
600/316

(Continued)

FOREIGN PATENT DOCUMENTS

DE    10 2006 052 125 A1    5/2007
WO    WO 2008/061788 A1    5/2008

OTHER PUBLICATIONS

International Search Report of PCT/EP2012/001637, Dec. 6, 2012.

*Primary Examiner* — Robert N Wieland
(74) *Attorney, Agent, or Firm* — Collard & Roe, P.C.

(57) ABSTRACT

The invention relates to a diagnostic measuring apparatus for non-invasively detecting at least one physiological parameter of the human body. The measuring apparatus comprises: —a continuum emitter (110) for emitting first electromagnetic radiation, the spectrum of which has a continuum extending over a wavelength range, —a bearing area for bearing a human body part (100) on the measuring apparatus, wherein the bearing area is designed such that the body part (100) is irradiated with the first electromagnetic radiation, wherein the first electromagnetic radiation is emitted by transmission, scattering and/or reflection as second electromagnetic radiation from the tissue of the body part (100), —a detector (102; 104) for detecting at least one spectral component of the second electromagnetic radiation, —a spectral decomposition unit (106; 114; 116; 402) for spectrally selecting wavelength ranges of the first and/or second electromagnetic radiation. Moreover, the invention relates to a diagnostic measuring apparatus for non-invasively detecting at least one physiological parameter of the human body, comprising: —a sensor having a matrix-shaped arrangement of measuring electrodes for carrying out an electrolyte movement measurement and a signal processing device connected to the sensor, wherein the signal processing device is designed to carry out a spatially and temporally resolved measurement of electrical potential values at the surface of a human body part via the sensor.

29 Claims, 7 Drawing Sheets

(56) References Cited

U.S. PATENT DOCUMENTS

Figure 1A:
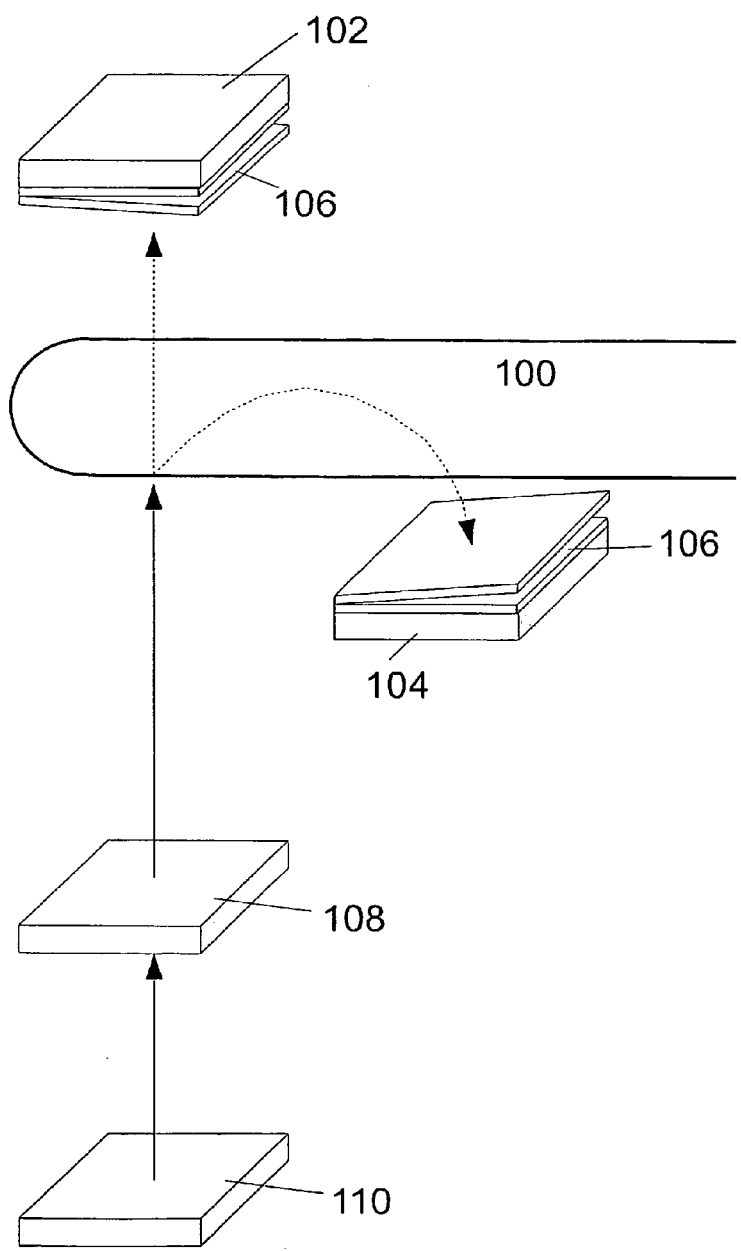

| | | |
|---|---|---|
| 7,555,102 B1 | 6/2009 | Renard-Le Galloudec et al. |
| 2002/0009251 A1* | 1/2002 | Byrne .................. G02F 1/0316 385/2 |
| 2005/0016947 A1* | 1/2005 | Fatke ................ H01J 37/32935 216/2 |
| 2005/0277818 A1 | 12/2005 | Myers |
| 2008/0103373 A1 | 5/2008 | Matter et al. |
| 2009/0247840 A1* | 10/2009 | Blank ................ A61B 5/14532 600/310 |
| 2010/0056880 A1 | 3/2010 | Cho et al. |
| 2012/0253149 A1* | 10/2012 | Steuer ............... A61B 5/14546 600/322 |
| 2015/0190090 A1* | 7/2015 | Silverman ............. A61K 31/04 600/363 |

\* cited by examiner

DIAGNOSTIC MEASURING APPARATUS WITH INTEGRATED SPECTROMETER

CROSS REFERENCE TO RELATED APPLICATIONS

This application is the National Stage of PCT/EP2012/001637 filed On Apr. 16, 2012, which claims priority under 35 U.S.C. §119 of German Application No. 10 2011 017 064.2 filed on Apr. 14, 2011, the disclosures of which are incorporated by reference. The international application under PCT article 21(2) was not published in English.

The invention relates to a diagnostic measuring apparatus for non-invasive detection of at least one physiological parameter of the human body.

It is known that supplying body tissue with oxygen is one of the most vital functions of human beings. For this reason, oximetric diagnosis modalities are of great importance in medicine. What are called pulse oximeters are routinely used. Such pulse oximeters typically comprise two light sources that radiate light at discrete wavelengths, namely red and infrared light, respectively, into the body tissue. The light is scattered in the body tissue and partly absorbed. The scattered light is finally detected by means of a detector. For this purpose, the detector comprises a light sensor in the form of a suitable photo cell, for example. Typically, commercial pulse oximeters use light in the wavelength range of 660 nm, for one thing. In this range, the light absorption of oxyhemoglobin and deoxyhemoglobin is greatly different. Accordingly, the intensity of the scattered light detected by means of the photo sensor varies as a function of how strongly the body tissue being examined has oxygen-rich or oxygen-poor blood flowing through it. For another, light in the wavelength range of 810 nm is usually used. This light wavelength lies in what is called the near infrared spectral range. The light absorption of oxyhemoglobin and deoxyhemoglobin is essentially the same in this spectral range. The hemoglobin oxygen saturation in arterial ($SaO_2$, $SpO_2$) and venous blood ($ScvO_2$, $SvO_2$) is generally measured with such apparatuses. The known pulse oximeters are furthermore able to generate a plethysmographic signal, i.e. a volume pulse signal, which reproduces the amount of blood in the microvascular system being detected by the pulse oximeter, which amount changes during the heartbeat (called photo-plethysmography). The usual pulse oximeters are placed either on the fingertip of a patient or also on the earlobe. Then the volume pulse signal from the blood perfusion of the microvascular system in these regions of the body tissue is generated.

For example, DE 10 2006 052 125 A1 discloses an apparatus for optical determination of physiological variables in perfused tissue. For this purpose, the apparatus has a first and a second light source, which emit light radiation of a first and a second wavelength, respectively, which can be predetermined, in each instance. Different physiological variables are determined by way of an evaluation unit and a photodetector, from the light that passes through the tissue and the light that is reflected by the tissue, respectively.

An apparatus for determining the oxygen saturation in the microcirculation ($StO_2$), i.e. where oxygen is exchanged with the tissue cells, is known from US 2005/0277818 A1. For this purpose, the apparatus comprises a plurality of light sources in the form of LEDs, which emit light at different wavelengths selected in targeted manner (e.g. 692 nm, 720 nm, 732 nm, 748 nm, 760 nm, 788 nm). The second derivation of the absorption spectrum is estimated from the intensity of the scattered or transmitted light detected at the different wavelengths, in accordance with a mathematical formula. A conclusion concerning the hemoglobin oxygen saturation $StO_2$ can then be drawn from the characteristics of this derivation spectrum ([in English:] "$2^{nd}$ derivative attenuation spectrum").

The approaches described above have the disadvantage that a special light source and, if necessary, a corresponding special light sensor must be provided separately for each wavelength. Estimation of the derivation spectrum according to US 2005/0277818 A1 mentioned above, on the basis of measurements at only a few wavelengths, is comparatively imprecise and accordingly leads to a not very precise determination of $StO_2$, in disadvantageous manner.

The invention is based on the task of making available an apparatus for non-invasive determination of physiological parameters that is improved as compared with the state of the art and expanded in terms of its functionality.

The task on which the invention is based is accomplished with the characteristics of the independent claim. Preferred embodiments of the invention are indicated in the dependent claims.

The invention proposes a diagnostic measuring apparatus that has a radiation source for emitting a first electromagnetic radiation. Preferably, the radiation source is a continuum emitter, the radiation spectrum of which has a continuum that extends over a wavelength range. In place of multiple light sources that emit (more or less narrow-band) electromagnetic radiation at a discrete wavelength, the continuum emitter can be used as a single light source, according to the invention, which covers a broad wavelength range, namely all the wavelengths required for the measurement, in each instance. The continuum emitter can be a light source that emits white light, for example. The apparatus according to the invention has a contact surface for placement of a human body part. The contact surface is configured in such a manner that the body part is irradiated with the first electromagnetic radiation. The electromagnetic radiation is scattered and/or reflected in the tissue of the body part irradiated in this manner. The radiation modified in this manner is referred to as a second electromagnetic radiation, in the sense of the invention, which is emitted by the tissue of the body part. A detector is provided, which detects at least a spectral component of the second electromagnetic radiation. For this purpose, the detector can have one or more suitable photosensors. Furthermore, the apparatus according to the invention comprises a spectral splitting unit for spectral selection of wavelength ranges of the first and/or second electromagnetic radiation. In the case of spectral selection of wavelengths of the first electromagnetic radiation, the contact surface of the apparatus according to the invention is disposed in such a manner that irradiation of the body part takes place at the spectrally selected wavelengths. In the case of spectral selection of wavelengths of the second electromagnetic radiation, the detector is configured for spectrally selective detection of the second electromagnetic radiation. The spectral splitting unit, in combination with the continuum emitter and the detector, thereby essentially forms a spectrometer with which the spectral range of interest can be measured completely and (quasi) continuously, specifically without restriction to individual discrete wavelengths. This is the essential advantage as compared with the state of the art.

In this connection, the measurements possible with the apparatus according to the invention comprise, without any restriction of generality, for example measurement of the intensity of the first electromagnetic radiation detected at the detector, without a body part lying against it—this measurement is helpful and can be necessary for calibration, and can take place at every wavelength, determination of the oxygen saturation $SaO_2$ at wavelengths 660 nm or 880 nm, respectively, and 810 nm, determination of the oxygen saturation in the tissue $StO_2$ at wavelengths in the range of 400 nm to 1000 nm, determination of the metabolism-induced local oxygen consumption at wavelengths in the range of 660 nm to 880 nm, perfusion measurement (volume pulse, pulse wave velocity, vascular stiffness index SI) at wavelengths from 660 nm to 880 nm, measurement of the water content in the skin at a wavelength of 940 nm, measurement of skin layer thickness, base blood amount, and blood density.

Both the skin layer thickness and the base blood amount are important parameters, in connection with other measurements, because the transmission and absorption of light in the skin is dependent not only on wavelength but also on layer thickness.

As is evident from the examples indicated above, the spectral breadth of the continuum of the first electromagnetic radiation should amount to at least 200 nm in the apparatus according to the invention. The spectral continuum of the first electromagnetic radiation should cover a wavelength range of 700 nm to 900 nm, if possible, preferably of 500 nm to 1000 nm, particularly preferably of 300 nm to 1100 nm, in order to be able to perform all the optical measurements of interest, without restrictions.

It should be pointed out that scattering of electromagnetic radiation in the sense of the invention is also understood to be intensity losses due to absorption processes in the tissue, as well as any types of photon/atom and photon/molecule interactions, including all types of elastic, non-elastic scattering and of resulting photon emissions (including fluorescence).

According to one embodiment of the invention, the spectral splitting unit separates the wavelength ranges covered by the first and/or second electromagnetic radiation spatially. Accordingly, the spectral splitting unit can be a refraction grating, a prism, an interference wedge or something similar.

According to one embodiment of the invention, the detector is furthermore configured for spatially resolved (and temporally resolved) detection of at least one spectral component of the second electromagnetic radiation. For one thing, this allows separate detection of physiological parameters with regard to different locations within the body tissue. In combination with the spatial separation of the wavelength ranges covered by the first and/or second electromagnetic radiation by means of the spectral splitting unit, the spatially resolving detector forms a spectrometer, with which a plurality of different wavelength ranges can be detected at the same time.

According to a preferred embodiment of the invention, the detector can have a pixel matrix of spatially separate photosensitive detector elements for spatially resolved (and temporally resolved) detection. For example, a semiconductor chip having an integrated matrix of photodetectors (e.g. CMOS line sensor) or also a CCD element is suitable. Each pixel can be assigned to a specific wavelength range. For example, a prism or an interference wedge can be disposed directly above the pixel matrix, so that the spectrally selected radiation gets to the pixels provided for the wavelength ranges, in each instance.

According to a further embodiment of the invention, the detector is furthermore configured to carry out a bio-impedance measurement and/or to carry out an electrolyte movement measurement.

For the determination of physiological parameters, such as body fat content, for example, the principle of bio-electrical impedance measurement (abbreviated bio-impedance measurement) is known. For the determination of the local oxygen consumption, for example, the capillary oxygen saturation in the tissue of the body part being examined can also be determined, in addition to the optically determined arterial oxygen saturation, by means of the measuring apparatus according to the invention. For this purpose, it is helpful if the composition of the body tissue being examined is known. Decisive parameters are the local fat content and/or the water content of the body tissue. These parameters can be detected by means of a bio-electrical impedance measurement. Furthermore, the electrical resistances of the body parts and of the blood vessels can be determined. According to a practical embodiment of the invention, optical measurements are thus combined with measurements of bio-impedance, in one apparatus. The bio-impedance measurement can furthermore be used to detect global tissue parameters, such as the global fat content and/or the global water content. In this way, the functionality of the measuring apparatus according to the invention is expanded. The sensors for the bio-impedance measurement can be configured in such a manner that not only local but also global tissue parameters can be measured using them.

Sodium-potassium-ATPase (more precisely: $3Na^+/2K^+$-ATPase), also referred to as sodium-potassium ion pump, is a transmembrane protein anchored in the cell membrane of tissue cells. The enzyme catalyzes the transport of sodium ions out of the call and the transport of potassium ions into the cell, under the hydrolysis of ATP, the energy carrier of human metabolism, specifically counter to the chemical concentration gradients and the electrical charge gradients. The cations $Na^+/K^+$ are distributed unevenly in the individual tissue cells: The $Na^+$ concentration in the interior of the cell is low (5-15 mmol/l); the $K^+$ concentration in the interior is high (120-150 mmol/l). This concentration gradient, which is of vital importance, is brought about, on the one hand, by what are called potassium channels, and on the other hand by the aforementioned sodium-potassium-ATPase. By means of sodium-potassium-ATPase, three $Na^+$ ions are conveyed to the outside and two $K^+$ ions are conveyed to the inside per ATP molecule. In this way, the electrical rest membrane potential that is functionally important, particularly for nerve and muscle cells, is obtained. The electrolyte movement measurement provided according to the invention, i.e. detection of the dynamics of the ion transports in the body cells as described above, thereby permits conclusions concerning the local metabolic activity and thereby—ultimately—concerning the state of health of the patient being examined.

According to a preferred embodiment of the invention, spatially resolved (and temporally resolved) detection of electrical potentials and current takes place by way of the surface of the body part being examined. This advantageously allows not only the electrolyte movement measurement that was described, but also the determination of body fat, the measurement of extracellular and intracellular mass and of the water proportion, in each instance, using depth profile analysis, proceeding from the body surface by way of the capillary tissue all the way into the interior.

According to one embodiment of the invention, detection of the bio-impedances and/or implementation of the electrolyte movement measurement take(s) place by means of a common sensor.

Likewise, separate sensors can be provided. The apparatus according to the invention can furthermore have sensors for recording the temperature of the body part and/or for recording an electrocardiogram, in addition to the optical sensors.

The bio-impedance measurement and/or the electrolyte movement measurement can take place in combination with the optical measurement or independent of the latter, using an apparatus according to the invention that has been equipped accordingly. A suitable apparatus has a sensor having a matrix-shaped arrangement of measuring electrodes for carrying out the electrolyte movement measurement, and a signal processing device connected with the sensor, whereby the signal processing device is set up for carrying out a spatially resolved and temporally resolved measurement of electrical potential values at the surface of a human body part, by way of the sensor. In this manner, the local potentials and currents and their dynamics can be recorded, in order to draw conclusions concerning the activity of the sodium-potassium ion pump and thereby concerning the local metabolism. The measurement of the electrical potential values for the electrolyte movement measurement can take place, in contrast to the usual bio-impedance measurement, without applying an external electrical current to the body part. The signal-emitting current or the corresponding potentials result from the ion movement itself. For this reason, the electrolyte movement measurement according to the invention can also be referred to as "ionetics" or [in English] "ionetics".

The bio-impedance measurement and the electrolyte movement measurement can take place by means of a single sensor. This can be made possible in that the sensor is switched sequentially, in order to thereby measure bio-impedances with spatial resolution (and time resolution) when current is applied, for one thing, and for another, to carry out the electrolyte movement measurement when no current is applied.

The dimensions of the surface of the sensor that enters into contact with the body part during the electrolyte movement measurement, according to the invention, typically amount to less than 15 mm by 15 mm, preferably less than 5 mm by 5 mm, particularly preferably less than 500 µm, by 500 µm. At the surface of the sensor, at least 4, preferably at least 16, further preferably at least 32, particularly preferably at least 64 measuring electrodes should be disposed, in order to achieve sufficient resolution. It is practical if the measuring electrodes are integrated into the surface of a semiconductor chip. In view of the typical time scales of the electrolyte dynamics of interest, the signal processing device should be set up for digitalization of the potential values at a sampling frequency of at least 10 kHz, preferably at least 1 MHz.

In a preferred embodiment of the apparatus according to the invention, the latter has a sensor for detecting the contact pressure with which the human body part lies against the contact surface of the measuring apparatus. In this embodiment, the contact pressure is measured in the region in which the body part is placed against the apparatus, for example by means of a pressure or force sensor disposed in the region of the contact surface. In this way, it is possible to guarantee a specific contact pressure that is required or optimal for detection of the at least one physiological parameter, if possible over the entire duration of the measurement, for example by monitoring it by means of the pressure or force sensor. In addition or alternatively, the measured contact pressure can be used for correction of the recorded data, if it is known in what manner the contact pressure influences data collection. Furthermore, the pressure sensor can be used as a diagnostic sensor unit. Thus, is it possible, for example using a sufficiently precise pressure sensor, to record the pulse progression and to utilize these data for non-invasive determination of physiological parameters.

It is particularly advantageous if the detector of the apparatus according to the invention, in addition to the pixel matrix mentioned above, composed of photodetectors, simultaneously has a matrix of measuring electrodes for the bio-impedance measurement and/or electrolyte movement measurement. It is practical that both measurement modalities can be integrated into a single semiconductor chip. This chip can comprise rows (or columns) of photodetectors connected with one another by way of shift registers, in an alternating arrangement, at its surface, similar to a CCD chip, and rows of pixel-like measuring electrodes for a corresponding potential measurement, also connected with one another by way of shift registers.

In total, a single multi-functional detector can be used for the apparatus according to the invention, which detector is able to carry out not only bio-impedance measurements and electrolyte movement measurements, but also optical measurements.

It is particularly advantageous if the apparatus according to the invention comprises the measurement modalities mentioned above in combination. In this way, a plurality of physiological parameters can be determined using a single apparatus, which significantly increases the possibility of a reliable conclusion concerning the state of health of the patient.

According to a possible embodiment of the invention, the spectral splitting unit for spectral selection of wavelength ranges has an interference wedge and/or a refraction grating and/or an interferometer. The selection of the suitable spectral splitting unit depends on various factors. As was already mentioned above, the use of an interference wedge is a particularly preferred embodiment, because it makes it possible, in simple manner, to carry out a plurality of measurements at different wavelengths, in parallel. The same holds true for using a refraction grating. If, on the other hand, an interferometer is used as the spectral splitting unit, this must be tuned so that different spectral ranges are sampled sequentially.

According to another embodiment of the invention, the evaluation of the electromagnetic radiation detected by the detector comprises a running time measurement of the electromagnetic radiation. In this way, a depth profile analysis is particularly possible. For this purpose, the continuum emitter should be operated in pulsed manner. A conclusion concerning the distance traveled in the tissue can be drawn from measuring the running time of the light pulse, and thereby concerning the tissue layers recorded, in each instance.

According to a further embodiment of the invention, the apparatus furthermore has an electronic evaluation unit as well as an integrated display unit for making the recorded and evaluated data available visually. In this way, an apparatus can be created, in total, which can be used in simple manner.

According to a further embodiment of the invention, the apparatus comprises a communications interface. For example, this can be a near-field and/or far-field communications interface (infrared, Bluetooth, GSM, UMTS, WiFi, LTE, etc.) or a USB interface. In all cases, communication can be carried out with central data processing systems, in order to allow central data evaluation and data storage, for example.

Figure 1B:
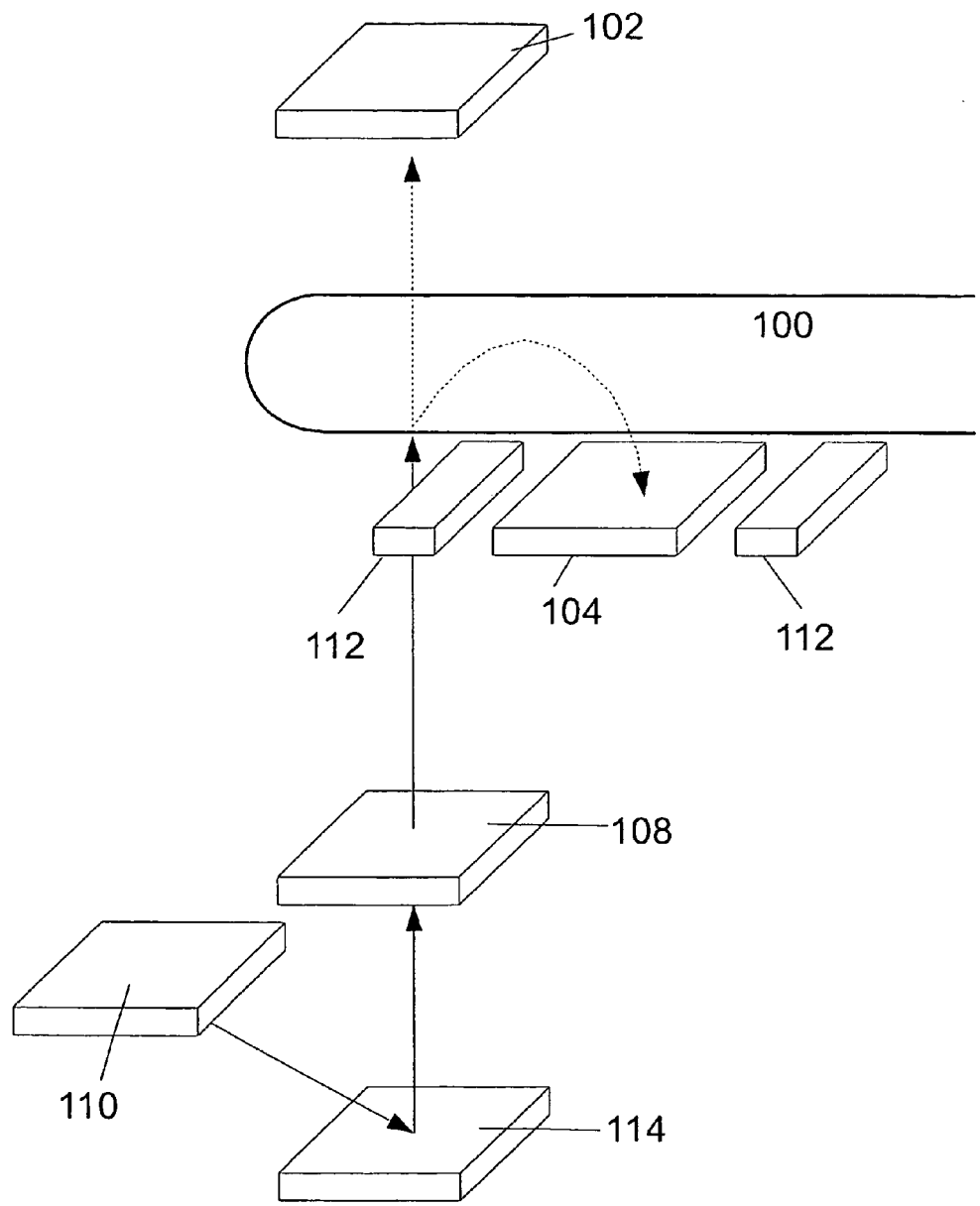
Figure 1C:
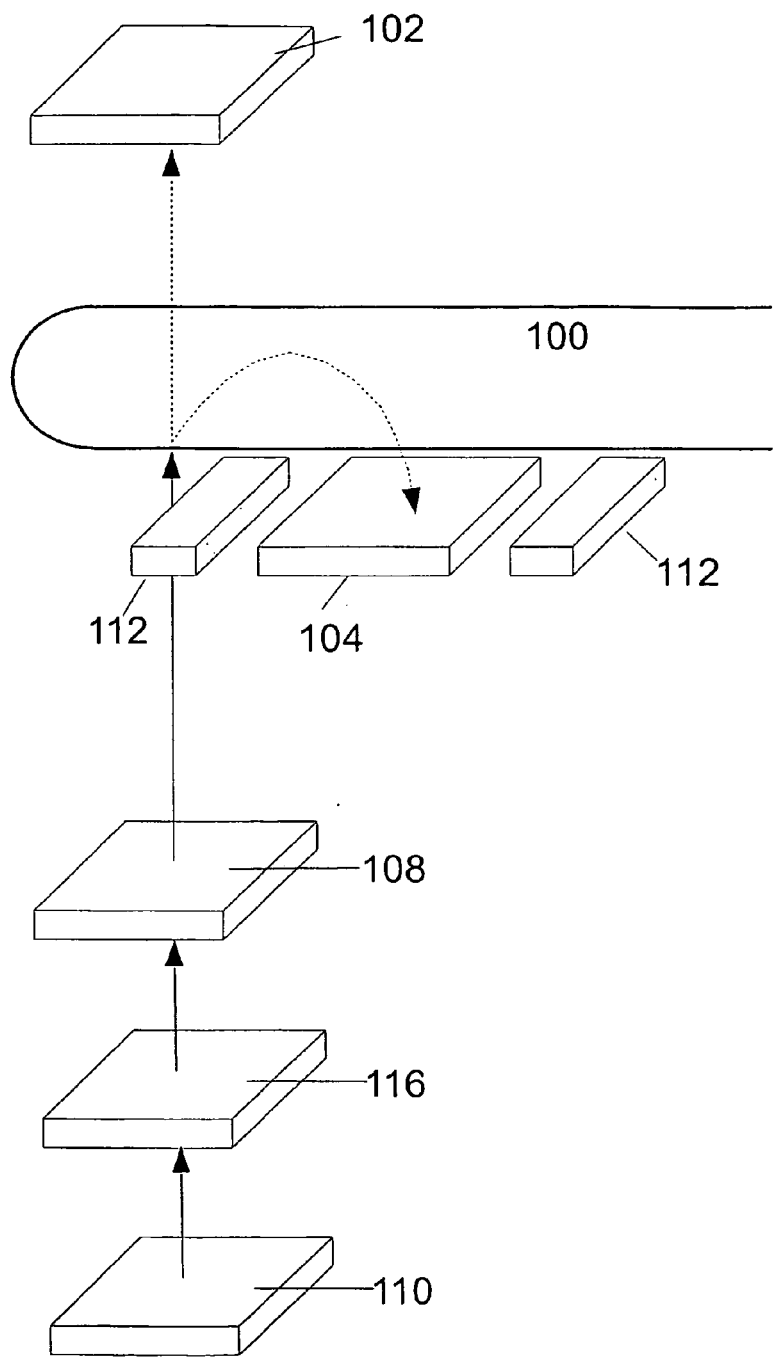
Figure 2A:
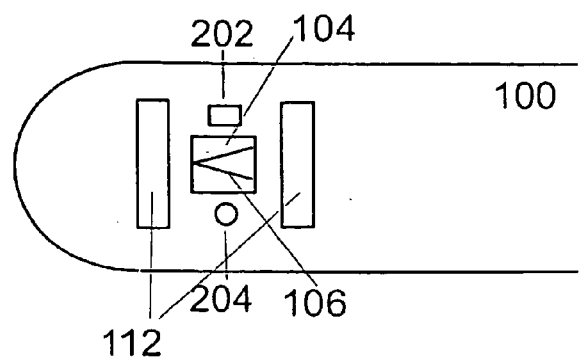
Figure 2B:
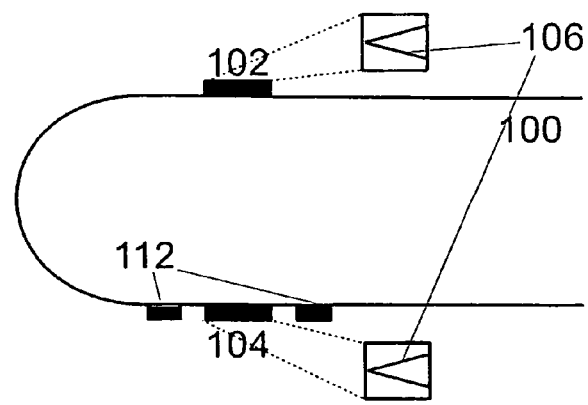
Figure 2C:
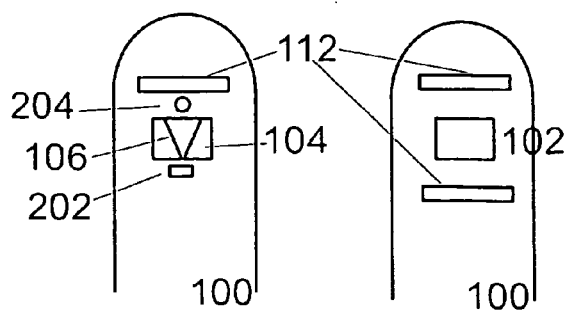
Figure 3:
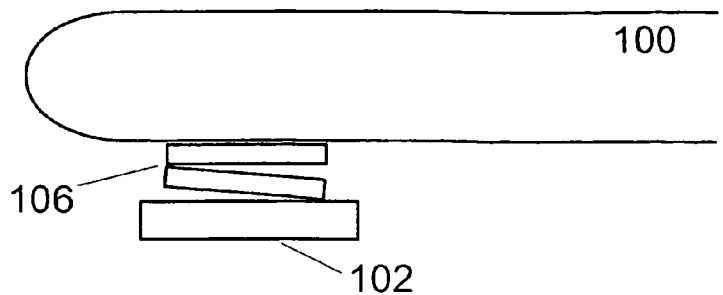
Figure 4A:
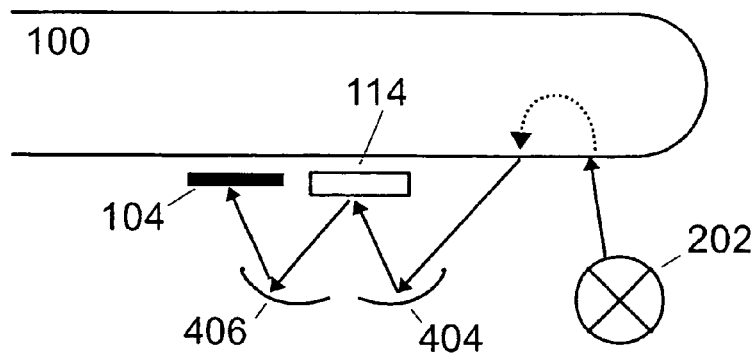
Figure 4B:
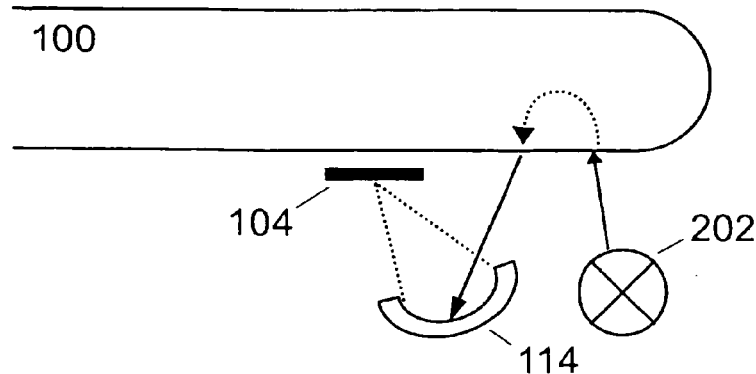
Figure 4C:
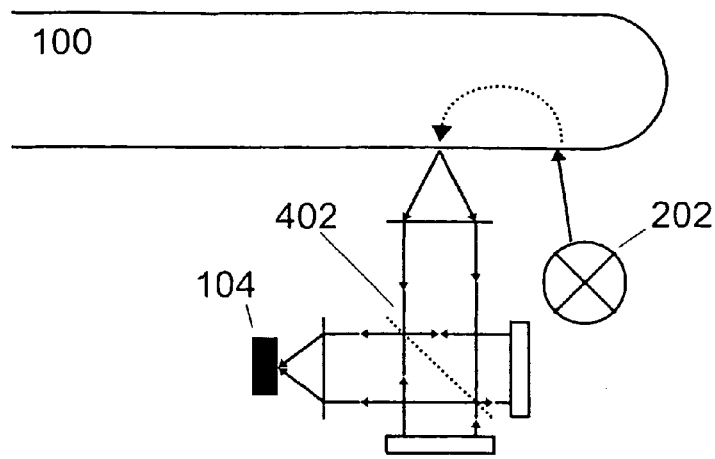
Figure 5:
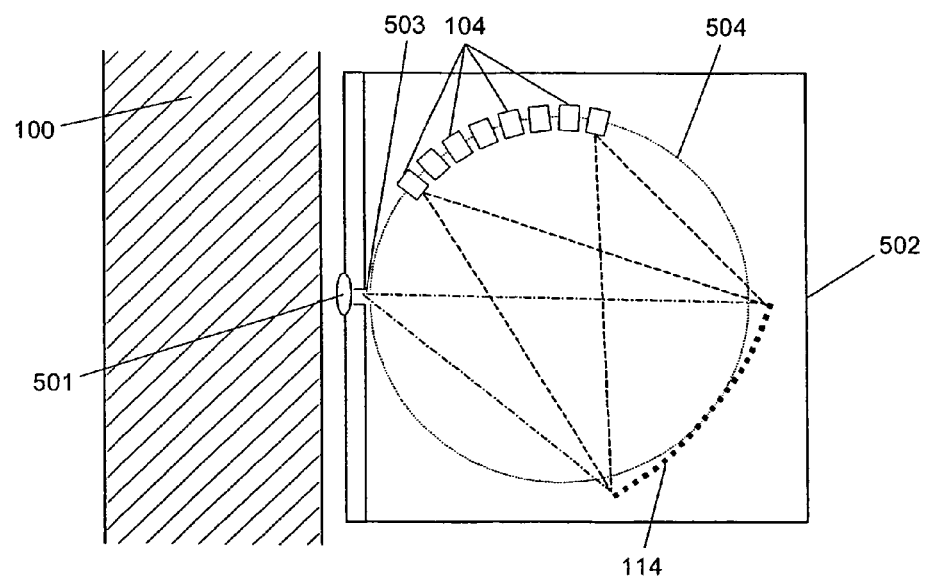

In the following, exemplary embodiments of the invention will be explained in greater detail using the drawings. These show:

FIG. 1a: schematic representation of the principle of functioning of the measuring apparatus according to the invention with a spectral splitting unit disposed directly on a detector, FIG. 1b: schematic representation of the principle of functioning of the measuring apparatus according to the invention with a variant of the placement of a spectral splitting unit, FIG. 1c: schematic representation of the principle of functioning of the measuring apparatus according to the invention with a further variant of the placement of a spectral splitting unit, FIG. 2a: schematic representation of the sensor system of the measuring apparatus according to the invention, from a view from an underside of a finger, FIG. 2b: schematic representation of the sensor system of a measuring apparatus according to the invention from a side view of a finger, FIG. 2c: schematic representation of a sensor system of the measuring apparatus according to the invention with structure for a finger from a left hand and also with structure for a finger from a right hand, FIG. 3: a detail view of the optical detector with spectral splitting unit, FIG. 4a: an optical sensor system of the measuring apparatus according to the invention, with a first variant of a reflection configuration, FIG. 4b: an optical sensor system of the measuring apparatus according to the invention with a second variant of a reflection configuration, FIG. 4c: an optical sensor system of the measuring apparatus according to the invention with a third variant of a reflection configuration, FIG. 5: Rowland spectrometer with optical detectors and gratings, and FIG. 6: exemplary embodiment of a sensor according to the invention.

In the following, elements that are similar to one another are identified with the same reference symbols.

FIG. 1 illustrates the principle of function of the measuring apparatus according to the invention in different embodiments. In FIGS. 1a-1c, a human body part 100 in the form of a finger, for example, can be seen, in each instance, whereby a continuum emitter 110 for emitting a first electromagnetic radiation is used to irradiate the body part 100 with broad-band (e.g. white) light. For example, the continuum emitter 110 is a semiconductor (one or more LED chips, possibly in combination with fluorescent or chemiluminescent pigments) as an emitter, whereby pulsed operation, operation modulated in some other way, or permanent operation are possible as operation modes. The continuum emitter 110 emits in broad-band manner, in the wavelength range of 300 nm to 1100 nm. The continuum emitter 110 should emit the first electromagnetic radiation with interference capability, if at all possible.

Furthermore, in FIGS. 1a-1c, a transparent semiconductor component 108 is used as an "imaging lens," in each instance. A semiconductor detector, preferably having a pixel matrix of discrete photodetectors, serves as the detector 102.

In the embodiment of FIG. 1a, spectral splitting of light takes place using interference wedges 106, which are affixed directly to corresponding detector chips having pixel matrices. The first electromagnetic radiation is emitted by the continuum emitter 110, transmitted through the imaging lens 108, and thereupon impacts the body part (e.g. finger) 100 that lies against the apparatus. In the tissue of the body part 100, the first electromagnetic radiation is emitted from the tissue of the body part 100 once again, by means of scattering and/or reflection.

Now two different measuring methods are used in parallel. The first measuring method works in transmission, i.e. an upper semiconductor detector in the form of the pixel matrix 102 is used, whereby this detector 102 detects the light transmitted through the sample. In this connection, the interference wedge 106, which brings about spectral splitting of the light transmitted through the sample 100, is disposed directly on the detector 102. The pixel matrix 102 thereby allows spectrally resolved detection of the second electromagnetic radiation, specifically simultaneously, at a plurality of different wavelengths, corresponding to the number of irradiated pixels. The second measuring method works in the reflection direction. For this purpose, a further semiconductor detector 104—also having a pixel matrix—is provided. First electromagnetic radiation emitted by the continuum emitter 110 again falls on the body part 100, is reflected and scattered from there, whereby the light emitted back from the body part 100 as second electromagnetic radiation is detected by the detector 104. An interference wedge for spectral splitting (interference wedge 106) is once again disposed directly on the detector 104, thereby making it possible to detect a plurality of different light wavelengths in parallel.

In FIG. 1a, no optional electrodes for a bio-impedance measurement are shown, but these can easily be implemented. In this case, the detectors 102 and 104, respectively, serve not only for detecting light but also for measuring impedance.

In place of the interference wedge, a refraction grating 114 is used in FIG. 1b. Light therefore falls on the refraction grating 114, proceeding from the continuum emitter 110, thereby bringing about spectral splitting of the light emitted by the continuum emitter 110. After spectral splitting, transmission of the light through the imaging lens 108 once again takes place, whereupon light detection in transmission or reflection, respectively, can be carried out by means of the detectors 102 or 104, respectively.

In FIG. 1b, electrodes 112 for current application for the purpose of bio-impedance measurements are shown as examples. The semiconductor detector 104 with pixel matrix serves not only for optical measurement but also for bio-impedance measurement here.

In FIG. 1c, finally, spectral splitting of the first electromagnetic radiation, i.e. of the light emitted by the continuum emitter 119, takes place using a transmission grating 116. Light is emitted by the continuum emitter 110, transmitted through the transmission grating 116, and, in this connection, split spectrally. Thereupon the spectrally split light once again transmits through the imaging lens 108, and finally, after scattering and reflection in the tissue of the body part 100, falls onto the detectors 102 and 104, respectively.

The electrodes 112 for the purpose of applying current for bio-impedance measurements are shown once again in FIG. 1c.

In FIGS. 1a-1c, the spectral splitting units (interference wedge, refraction grating, transmission grating) are optimized, in each instance, in order to bring about spectral splitting over the wavelength range of 300 m to 1100 nm.

FIG. 2 schematically shows the sensor concept according to the invention.

A view of the underside of the finger is shown in FIG. 2a, and a side view of the finger is shown in FIG. 2b.

Fundamentally, a configuration is used here that was discussed above with regard to FIG. 1a (interference wedge solution).

The finger 100 lies on the detector 104 with its underside, whereby the interference wedge 106 for spectral splitting is disposed between finger 100 and detector 104. A radiation outlet 202 is disposed in the contact surface (not shown) for the finger 100. From there, the first electromagnetic radiation from the continuum emitter is guided onto the finger 100, whereby light reflected by the finger 100, i.e. the second electromagnetic radiation, is detected by means of the detector 104.

The electrodes 112 once again serve for applying current for a bio-impedance measurement, whereby additionally, a temperature sensor 204 (for example a thermistor) is provided for measuring the body temperature.

As can be seen in FIG. 2b, the detector 104 is disposed on the underside of the finger, whereby the detector 102 is situated on the top of the finger. The detector 102 serves for measuring the light in transmission, whereby the interference wedge 106 is once again disposed between the top of the finger and the detector.

In FIG. 2c, finally, the detection part of the diagnostic measuring apparatus is shown schematically, separately for a finger of the left hand (left half of the picture) and a finger of the right hand (right half of the picture). The electrodes 112 are provided for bio-impedance measurements and for recording of electrocardiograms (hand-to-hand measurement). The semiconductor detector 104 with interference wedge 106 on the left finger serves for spectrally resolved optical measurement. The detector 102 with pixel matrix on the right finger also serves for bio-impedance measurements, and for measurements of the local electron movement ("ionetics," see above).

FIG. 2c illustrates the overall concept of the sensor system of the measuring apparatus according to the invention. Global bio-impedance measurement and EKG measurement are combined with local bio-impedance measurement and electrolyte movement measurement. In addition, there are a spectrally split optical measurement and a temperature measurement. Integrated sensors with a pixel matrix on a semiconductor basis are used for the optical measurement and the local bio-impedance measurement and electrolyte movement measurement. The entire sensor system, including the related electronic circuits and the software for the signal processing and evaluation can be accommodated in ASIC modules. Therefore the total concept can be implemented with few components, in very compact and cost-advantageous manner.

The measurement results that can be obtained using the combination of measurement modalities as described can be combined in many different ways in order to be able to make comprehensive statements concerning the general state of health of the patient. Cardiac/cardiovascular function, respiration, and metabolism can be assessed equally, and also, statements concerning the status of the patient's vascular system can be made. Ultimately, the sensor system of the measuring apparatus according to the invention also makes it possible to determine the blood glucose level non-invasively, from the measurement data, by means of suitable evaluation. With regard to further details in this regard, reference is made to WO 2008/061788 A1.

FIG. 3 shows a detail view with semiconductor detector 102 and with spectral splitting unit in the form of an interference wedge 106. The interference wedge is disposed between body part 100 and detector 102, whereby the interference wedge 106 covers the pixel matrix of the detector 102, in terms of surface area. In this way, the pixel matrix of the detector 102 can detect different spectral components of the light proceeding from the tissue of the body part 100 at different positions underneath the interference wedge 106.

FIG. 4 shows different further variants of spectral splitting units that can be used according to the invention.

All the exemplary embodiments shown have in common that a continuum emitter is used for generating first electromagnetic radiation, whereby the radiation of this emitter is coupled into the body part 100 by way of a radiation outlet 202 integrated into the contact surface of the measurement apparatus. A measuring arrangement with a reflection configuration is shown in FIGS. 4a-4c, in each instance.

In FIG. 4a, a refraction grating 114 using reflection is used, whereby light reflected by the finger 100 first falls onto a concave mirror 404 and is parallelized in this manner. Thereupon the light falls onto the refraction grating 114, from where it falls onto the concave mirror 406, with spectral splitting. The mirror 406 then focuses the radiation for the different wavelength ranges of different pixels of the detector 104, in each instance. In total, the arrangement in FIG. 4a approximately corresponds to a "Czerny-Turner" spectrometer.

In FIG. 4b, a concave refraction grating 114 using reflection is used. Light is coupled into the body part 100 from the radiation outlet 202, is scattered and reflected there, and impacts the refraction grating 114 as second electromagnetic radiation. Thereupon the light is directly reflected onto the detector 104, with light refraction and thereby spectral splitting. This arrangement corresponds to a "Paschen-Runge" spectrometer.

Finally, FIG. 4c shows a third variant in which light from the radiation outlet 202 is coupled into the body part 100 as first electromagnetic radiation, and is thereupon scattered and reflected in the tissue. The second electromagnetic radiation emitted by the body part 100 in this manner is split into spectral components by means of an interferometer, for example a Michelson interferometer 402, in order to thereupon be detected by the detector 104.

The variant shown in FIG. 5 comes close to the exemplary embodiment in FIG. 4b. In FIG. 5, the radiation source or the radiation outlet is not shown. The radiation scattered and/or reflected in the body part 100 is focused onto the entry gap 503 of a Rowland spectrometer by means of a lens 501 that is integrated into a sensor housing 502. The entry gap 503 is situated on a circle 504 (Rowland circle), as are a spherically curved grating 114, the radius of curvature of which corresponds to the diameter of the Rowland circle, and the (one-dimensional) detector matrix 104. The electromagnetic radiation impacts the concave grating 114 through the entry gap 503, and there is split into the individual wavelengths that fall onto the individual photodetectors of the array 104, in each instance, which are disposed along the Rowland circle 504. The individual photodetectors (up to 100 or even up to 1000 of them) have such a small distance from one another that the entire spectrum can be recorded simultaneously, with a corresponding resolution. The grating 114 is essentially spherical, i.e. curved in two planes, in order to achieve focusing of the dispersed radiation onto the photodetector, and to avoid astigmatism. The spectrometer shown in FIG. 5 can advantageously be implemented in very compact manner.

Figure 6:
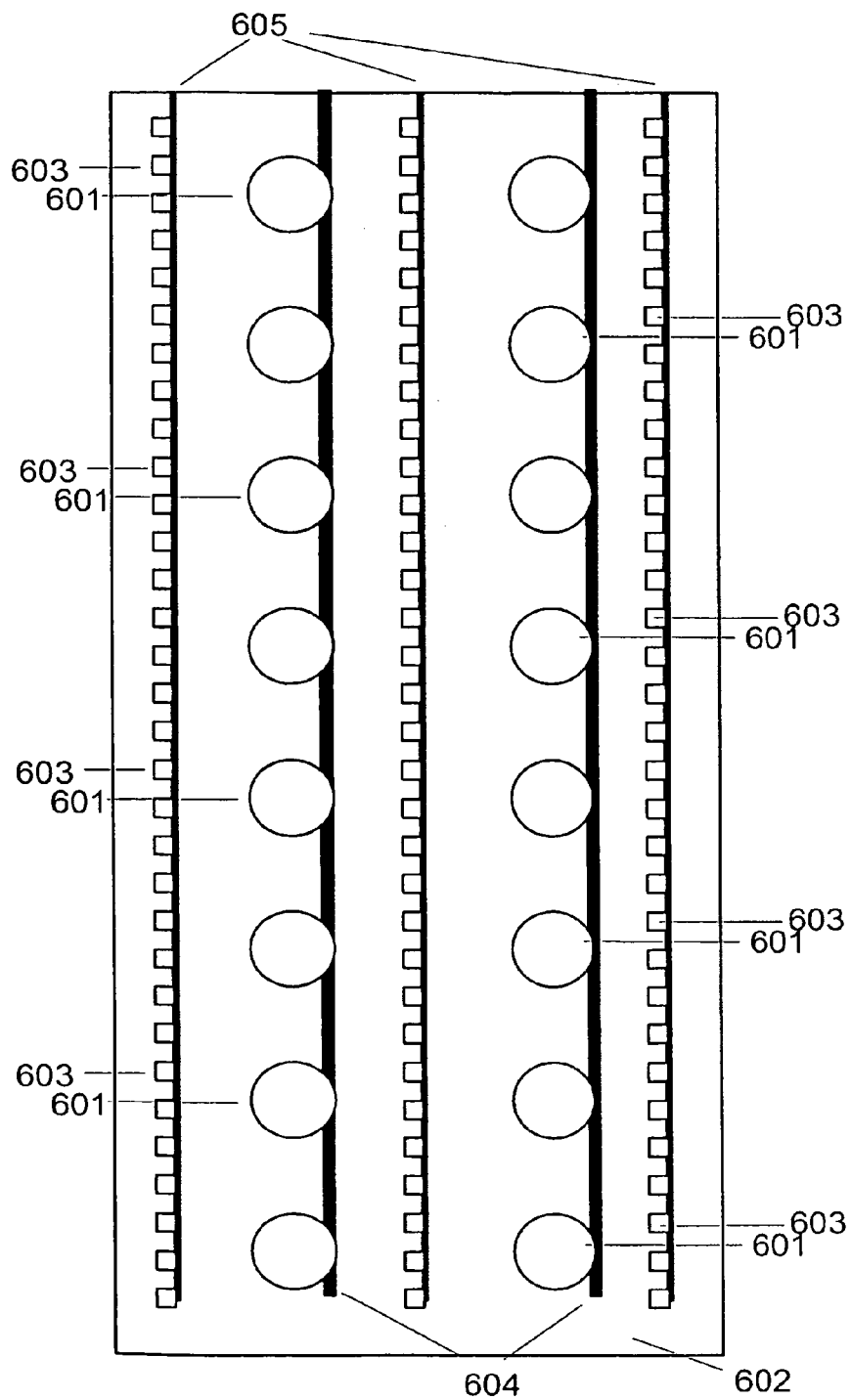

For the optical measurement and the local bio-impedance measurement and electrolyte movement measurement according to the invention, it is practical, as already mentioned above, if an integrated sensor having a pixel matrix on a semiconductor basis, for example using CMOS technology, is used. An exemplary embodiment of a corresponding sensor is shown in FIG. 6. The sensor has a matrix-shaped arrangement of measuring electrodes 601 in the form of metallic conical tips integrated into the surface of a semiconductor chip 602. These electrodes serve for spatially resolved and simultaneously temporally resolved measurement of electrical potentials on the body surface. Furthermore, a matrix-shaped arrangement of photodetectors 603 is provided for spatially resolved and temporally resolved measurement of electromagnetic radiation. The measuring electrodes 601 and the photodetectors 603 are disposed, in each instance, in rows, alternately on the surface of the semiconductor chip 602. In this connection, the photodetectors 603 of one row and the measuring electrodes 601 of another row are connected with one another by way of shift registers 604 and 605, respectively, in each instance. The measurement values recorded with the sensor can be continuously read out, in temporally resolved and spatially resolved manner, by way of a corresponding cycle control of the shift registers 604, 605. The sensor arrangement shown has the advantage that electrical potentials and electromagnetic radiation can be recorded simultaneously at the same measuring location, so that the recorded measurement values can be evaluated in combination, in order to obtain corresponding physiological parameters from them.

It should be pointed out that the invention can be used not just exclusively for human body parts in the form of fingers, but that the invention is also suitable for any desired body parts such as legs, arms or hands.

REFERENCE SYMBOL LIST 100 body part
102 detector
104 detector
106 interference wedge
108 imaging lens
110 emitter
112 electrode
114 refraction grating
116 transmission grating
202 radiation outlet
204 thermistor
402 interferometer
404 mirror
406 mirror
501 optics
502 sensor housing
503 entry gap
504 Rowland circuit
601 measuring electrodes
602 semiconductor chip
603 photo-detectors
604 shift register
605 shift register

The invention claimed is:

1. Diagnostic measuring apparatus for non-invasive detection of at least one physiological parameter of the human body, wherein in a common housing the apparatus comprises:
    a radiation source for emitting first electromagnetic radiation,
    a contact surface for placement of a human body part against the measuring apparatus, wherein the contact surface is configured in such a manner that irradiation of the body part with the first electromagnetic radiation takes place, wherein the first electromagnetic radiation is emitted from the tissue of the body part via scattering and/or reflection and/or transmission, as a second electromagnetic radiation,
    a detector for detection of at least one spectral component of the second electromagnetic radiation,
    a spectral splitting unit for spectral selection of wavelength ranges of the first and/or second electromagnetic radiation, wherein the detector is furthermore configured to carry out a bio-impedance measurement and/or to carry out an electrolyte movement measurement.

2. Apparatus according to claim 1, wherein the radiation source is a continuum emitter, wherein the spectrum of the first electromagnetic radiation has a continuum. that extends over a wavelength range.

3. Apparatus according to claim 1, wherein the spectral splitting unit spatially separates the wavelength ranges comprised by the first and/or second electromagnetic radiation.

4. Apparatus according to claim 1, wherein the detector is configured for spatially resolved detection of at least one spectral component of the second electromagnetic radiation.

5. Apparatus according to claim 4, wherein the detector has a pixel matrix of spatially separate detector elements for spatially resolved detection.

6. Apparatus according to claim 5, wherein the detector and the spectral splitting unit, together, form a Rowland spectrometer.

7. Apparatus according to claim 6, wherein the spectral splitting unit is a grating that has an essentially spherical curvature, so that the second electromagnetic radiation is dispersed by the grating and focused onto the detector elements.

8. Apparatus according to claim 1, furthermore having at least one sensor for recording the temperature of the body part and/or for recording an electrocardiogram and/or for recording bio-impedance values and/or for carrying out an electrolyte movement measurement.

9. Apparatus according to claim 8, wherein the detection of the bio-impedance values and/or the implementation of the electrolyte movement measurement takes place via a common sensor.

10. Apparatus according to claim 8, wherein the apparatus is set up for calculating
    the artery temperature and/or
    the average body temperature and/or
    the electrical resistances of body parts and/or blood vessels, and/or
    the body core temperature from the measurement signals of the sensor.

11. Apparatus according to claim 8, wherein the sensor is configured for spatially resolved detection of the bio-impedance values and/or for spatially resolved implementation of the electrolyte movement measurement.

12. Apparatus according to claim 11, wherein the sensor comprises a matrix-shaped arrangement of measuring electrodes.

13. Apparatus according to claim 1, wherein the spectral splitting unit has an interference wedge and/or a refraction grating and/or an interferometer for spectral selection of wavelength.

14. Apparatus according to claim 13, wherein the interference wedge is disposed directly above the detector.

15. Apparatus according to claim 1, wherein the spectral splitting unit can he spectrally tuned.

16. Apparatus according to claim 1, wherein the apparatus is set up for carrying out a running time measurement of the electromagnetic radiation detected by the detector.

17. Apparatus according to claim 1, wherein the spectral width of the first electromagnetic radiation amounts to at least 200 nm.

18. Apparatus according to claim. 1, wherein the spectrum of first electromagnetic radiation covers at least a wavelength range of 600 nm to 900 nm.

19. Apparatus according to claim 1, having;
a sensor having a matrix-shaped arrangement of measuring electrodes, and
a signal, processing device that is connected with the sensor, wherein the signal processing device is set up for carrying out a spatially resolved or temporally resolved measurement of electrical potential values at the of a human body part, by way of the sensor.

20. Apparatus according to claim 19, wherein the measurement of the electrical potential values takes place without applying an electrical current to the body part.

21. Apparatus according to claim 19, wherein the dimensions of the surface of the sensor that come into contact with the body part during the measurement amount to less than 15 mm by 15 mm.

22. Apparatus according to claim 21, wherein at least 4 measuring electrodes are disposed on the surface of the sensor.

23. Apparatus according to claim 21, wherein the measuring electrodes are integrated into the surface of a semiconductor chip.

24. Apparatus according to claim 19, wherein the signal processing device is set up for digitalizinq the potential values at a sampling frequency of at least 10 kHz.

25. Apparatus accordinq to claim 1, further comprising a sensor for detecting the contact pressure with which the human body part lies against the contact surface of the measuring apparatus.

26. Sensor for an apparatus according to claim 1, further comprising a matrix-shaped arrangement of measuring electrodes for spatially resolved measurement of electrical potentials, and a matrix-shaped arrangement of photodetectors for spatially resolved measurement of electromagnetic radiation.

27. Sensor according to claim 26, wherein the measuring electrodes and the photodetectors are integrated into the surface of a semiconductor chip.

28. Sensor according to claim 27, wherein the measuring electrodes and the photodetectors are disposed in rows or columns, in each instance, alternately, on the surface of the semiconductor chip.

29. Sensor according to claim 28, wherein the photodetectors of one row and the measuring electrodes of one row are connected with one another by way of shift registers, in each instance.

* * * * *